(12) United States Patent
Philbrick et al.

(10) Patent No.: US 11,423,384 B1
(45) Date of Patent: Aug. 23, 2022

(54) SYSTEMS AND METHODS FOR PAYMENT METHOD SELECTION

(71) Applicant: UNITED SERVICES AUTOMOBILE ASSOCIATION (USAA), San Antonio, TX (US)

(72) Inventors: Ashley Raine Philbrick, San Antonio, TX (US); Oscar Guerra, San Antonio, TX (US); Kelly Q. Baker, San Antonio, TX (US); Carlos J P Chavez, San Antonio, TX (US); Yevgeniy Viatcheslavovich Khmelev, San Antonio, TX (US); Theresa Marie Matowitz, San Antonio, TX (US)

(73) Assignee: United Services Automobile Association (USAA), San Antonio, TX (US)

(*) Notice: Subject to any disclaimer, the term of this patent is extended or adjusted under 35 U.S.C. 154(b) by 0 days.

(21) Appl. No.: 17/076,546

(22) Filed: Oct. 21, 2020

Related U.S. Application Data

(60) Provisional application No. 62/928,486, filed on Oct. 31, 2019.

(51) Int. Cl.

| | |
|---|---|
| *G06Q 30/00* | (2012.01) |
| *G06Q 20/22* | (2012.01) |
| *G06Q 20/36* | (2012.01) |
| *G06Q 20/40* | (2012.01) |
| *G06Q 30/02* | (2012.01) |
| *G06Q 40/00* | (2012.01) |
| *G16H 40/20* | (2018.01) |

(Continued)

(52) U.S. Cl.
CPC .......... *G06Q 20/227* (2013.01); *G06Q 10/10* (2013.01); *G06Q 20/367* (2013.01); *G06Q 20/4015* (2020.05); *G06Q 30/0201* (2013.01); *G06Q 30/0229* (2013.01); *G06Q 30/0236* (2013.01); *G06Q 30/0283* (2013.01); *G06Q 40/02* (2013.01); *G06Q 40/12* (2013.12); *G16H 40/20* (2018.01)

(58) Field of Classification Search
None
See application file for complete search history.

(56) References Cited

U.S. PATENT DOCUMENTS

| | | | | |
|---|---|---|---|---|
| 5,945,653 | A * | 8/1999 | Walker | G06Q 20/341 |
| | | | | 235/383 |
| 7,566,000 | B2 * | 7/2009 | Agostino | G06Q 30/02 |
| | | | | 235/383 |
| 10,409,783 | B1 * | 9/2019 | Miller | G06Q 10/0639 |

(Continued)

*Primary Examiner* — Luis A Brown
(74) *Attorney, Agent, or Firm* — Fletcher Yoder, P.C.

(57) ABSTRACT

An electronic device is disclosed that enables payment option selection by receiving a location of the electronic device from a location sensor and determines a retailer associated with the location. The electronic device stores a mobile wallet that in turn stores multiple payment options. The electronic device then determines discounts, rewards, or both, for the payment options, and compares the discounts, rewards, or both for the payment options to determine a recommended payment option. The electronic device enables selection of the recommended payment option to perform a transaction with the retailer, and performs the transaction using the recommended payment option in response to the selection of the recommended payment option.

20 Claims, 5 Drawing Sheets

(51) Int. Cl.
*G06Q 40/02* (2012.01)
*G06Q 10/10* (2012.01)

(56) References Cited

U.S. PATENT DOCUMENTS

| | | | | |
|---|---|---|---|---|
| 10,440,009 B1* | 10/2019 | Manwiller | ............... | H04L 63/10 |
| 10,699,289 B1* | 6/2020 | Dalton | ............... | G06Q 20/3221 |
| 2006/0113376 A1* | 6/2006 | Reed | ....................... | G06Q 20/04 |
| | | | | 235/383 |
| 2008/0154757 A1* | 6/2008 | Barros | ................... | G06Q 40/00 |
| | | | | 705/14.36 |
| 2010/0088149 A1* | 4/2010 | Sullivan | .................. | G06Q 30/06 |
| | | | | 705/16 |
| 2010/0250379 A1* | 9/2010 | Giordano | ............. | G06Q 20/00 |
| | | | | 705/20 |
| 2011/0191160 A1* | 8/2011 | Blackhurst | ............ | G06Q 20/40 |
| | | | | 705/14.38 |
| 2011/0231223 A1* | 9/2011 | Winters | ............. | G06Q 30/0201 |
| | | | | 705/14.1 |
| 2014/0070001 A1* | 3/2014 | Sanchez | ............. | G06Q 30/0233 |
| | | | | 235/380 |
| 2014/0074569 A1* | 3/2014 | Francis | ................. | H04L 63/083 |
| | | | | 705/14.3 |
| 2014/0172559 A1* | 6/2014 | Caiman | ............... | G06Q 20/3224 |
| | | | | 705/26.9 |
| 2014/0279474 A1* | 9/2014 | Evans | ................... | G06Q 20/40 |
| | | | | 705/41 |
| 2014/0379453 A1* | 12/2014 | Booth | .................... | G06Q 20/14 |
| | | | | 705/14.27 |
| 2015/0193827 A1* | 7/2015 | Pearson | ............. | G06Q 30/0222 |
| | | | | 705/14.66 |
| 2016/0180368 A1* | 6/2016 | Booth | ................ | G06Q 30/0238 |
| | | | | 705/14.27 |
| 2017/0053347 A1* | 2/2017 | Lipshitz | ............ | G06Q 30/0601 |
| 2017/0061461 A1* | 3/2017 | Jajara | ................... | G06Q 20/367 |
| 2017/0161825 A1* | 6/2017 | Nair | ................... | G06Q 30/0255 |
| 2017/0293901 A1* | 10/2017 | Savla | ..................... | G06Q 20/102 |
| 2018/0096323 A1* | 4/2018 | Baber | ..................... | G06Q 20/10 |
| 2018/0165703 A1* | 6/2018 | Oshry | ................... | G06Q 20/387 |
| 2019/0130432 A1* | 5/2019 | Unnerstall | ........... | G06Q 20/363 |
| 2019/0272537 A1* | 9/2019 | Miller | ................. | H04L 63/0428 |
| 2019/0295054 A1* | 9/2019 | Purves | .................... | G06Q 20/36 |
| 2019/0311360 A1* | 10/2019 | Miller | ................... | G06N 20/00 |
| 2020/0074433 A1* | 3/2020 | Chopra | ................. | G06Q 20/405 |
| 2020/0160368 A1* | 5/2020 | Miller | ................. | G06Q 20/351 |
| 2020/0286061 A1* | 9/2020 | Wang | ................... | G06Q 20/352 |
| 2021/0073838 A1* | 3/2021 | Verma | ................... | G06Q 40/12 |

* cited by examiner

US 11,423,384 B1

SYSTEMS AND METHODS FOR PAYMENT METHOD SELECTION

CROSS-REFERENCE TO RELATED APPLICATIONS

This application claims the benefit of U.S. Provisional Application Ser. No. 62/928,486, entitled "SYSTEMS AND METHODS FOR PAYMENT METHOD SELECTION," filed Oct. 31, 2019, which is hereby incorporated by reference in its entirety for all purposes.

BACKGROUND

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

The present disclosure relates generally to financial transactions, and more particularly to payment method selection. An electronic device may store and execute a mobile wallet software application that in turn stores multiple types of payment methods that may be used to perform financial transactions (e.g., purchase goods or services). The payment methods may include credit cards, debit cards, health savings accounts, and so on. When performing a financial transaction at a retailer, a payment method may offer incentives, in the forms of discounts and/or rewards, to use that particular payment method to perform the financial transaction. However, it is presently recognized that it may be difficult and/or tedious for a user to determine the best or a preferred incentive (e.g., the greatest discount and/or reward) among the multiple payment methods stored in the mobile wallet.

SUMMARY

These and other features, aspects, and advantages of the present disclosure will become better understood when the following detailed description is read with reference to the accompanying drawings in which like characters represent like parts throughout the drawings, wherein:

In one embodiment, a portable electronic device includes a location sensor that determines location data indicative of a location of the portable electronic device, and one or more memory devices and one or more processors. The one or more memory devices store a mobile wallet and instructions. The mobile wallet includes payment options, and the instructions, when implemented by the one or more processors, cause the one or more processors to access the location data, determine a retailer associated with the location data, and determine reward data associated with the payment options based on the retailer. The instructions also cause the one or more processors to compare the reward data for the payment options to determine a recommended payment option for the retailer from the payment options, enable selection of the recommended payment option to perform a transaction with the retailer, and perform the transaction using the recommended payment option in response to the selection of the recommended payment option.

In another embodiment, a system includes a payment option server having reward data for a payment option stored thereon, and an electronic device. The electronic device includes a location sensor that determines location data indicative of a location of the electronic device, and a controller having one or more memory devices and one or more processors. The one or more memory devices store a mobile wallet and instructions. The mobile wallet stores payment options, including the aforementioned payment option. The instructions cause the one or more processors to receive the location data determined via the location sensor, determine a retailer associated with the location data, and receive the reward data for the payment option from the payment option server. The instructions also cause the one or more processors to determine rewards for the payment options. The rewards are based at least in part on the reward data. The instructions further cause the one or more processors to compare the rewards for the payment options to determine a recommended payment option from the payment options, enable selection of the recommended payment option to perform a transaction with the retailer, and perform the transaction using the recommended payment option in response to the selection of the recommended payment option.

In yet another embodiment, one or more tangible, non-transitory, computer-readable media stores instructions that cause one or more processors to receive a location from a location sensor, determine a retailer associated with the location, and receive an indication that a transaction is to be performed with the retailer. In response to determining that the transaction includes medical goods or services, the instructions cause one or more processors to enable at least partial completion of the transaction related to the medical goods or services using a health savings account. In response to determining that the transaction is not completed, the instructions cause one or more processors to determine rewards for payment options stored in a mobile wallet, compare the rewards for the payment options to determine a recommended payment option from the payment options, and enable selection of the recommended payment option to perform a transaction with the retailer. The instructions also cause one or more processors to perform the transaction using the recommended payment option in response to the selection of the recommended payment option.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
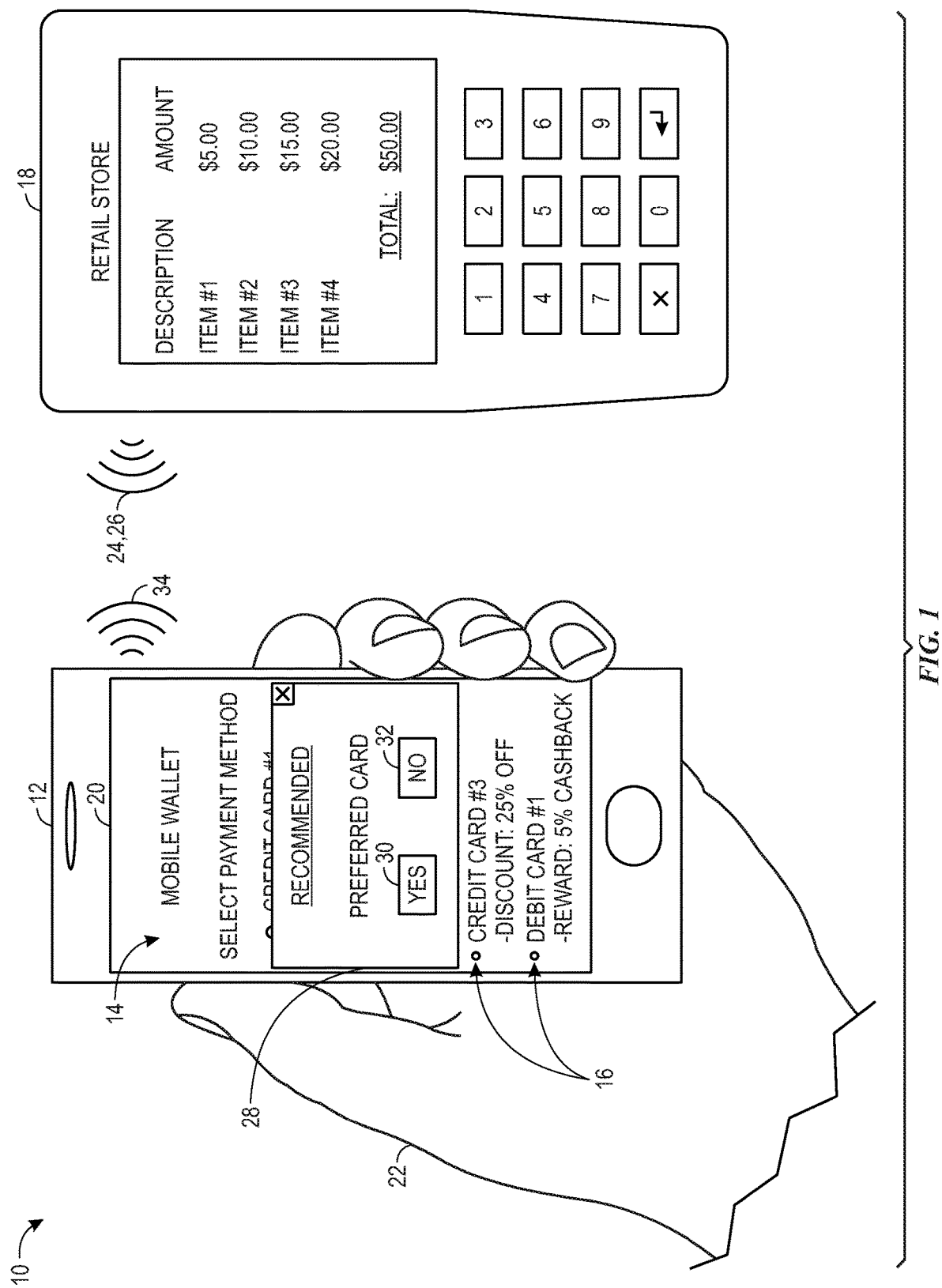
FIG. 1 illustrates a geolocation purchasing system, in accordance with embodiments described herein.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Mobile wallets are virtual wallets that store payment method information on a personal device. This payment method information, which may be referred to as payment options (e.g., credit card data, debit card data, bank account data, electronic fund transfer data), may include data to identify and authorize payment via an account (e.g., a credit card account). Generally, a mobile wallet is a software application that can be built-in or installed on a smartphone. The mobile wallet may store credit card information, debit card information, health savings account information, or other payment method information. A user may make payments to retailers (e.g., grocery stores, gas stations, restaurants) using a mobile wallet software application. To make a payment, the user may select a payment method (corresponding to payment method information or a payment option) and move the personal device proximate to a point-of-sale terminal (e.g., cash register). The mobile wallet application may use communication circuitry of the personal device to communicate the selected payment method information to the point-of-sale (POS) terminal. The POS terminal verifies the selected payment method information and performs the transaction. However, the selected payment method may not provide certain potential benefits to the user that, for example, other payment methods may provide. That is, some payment methods may provide discounts and/or rewards at a particular retailer. In other cases, some payment methods may provide discounts and/or rewards for certain goods or services. As the mobile wallet application merely provides a list of payment methods stored in the mobile wallet, the user may select a payment method that does not provide increased or optimum benefits (e.g., rewards and/or discounts) to the user, or at least notify the user of the increased or optimum benefits. It should be noted that a reward, as set forth by the present disclosure, broadly includes discounts, benefits, cash back, points, prizes, and so forth.

With the foregoing in mind, the present disclosure provides geolocation purchasing systems and methods having a personal device (portable device) that prompts a user to select a particular payment method (payment option) that benefits the user based on a location of the personal device (e.g., a retailer associated with the location of the personal device). In particular, the personal device determines one or more retailers located at or near a geolocation or geographic location of the personal device. Having identified a retailer, the personal device then determines rewards and discounts available for each payment method stored in a mobile wallet associated with the personal device at the identified retailer. That is, reward data (e.g., discount value, point amount, charitable contribution level) associated with use of a particular payment option at the retailer may be accessed by the personal device. The personal device analyzes the rewards and discounts to determine a particular payment method that provides the greatest benefit to the user or addresses a preference. The personal device then prompts the user, via a display of the personal device, to select the particular payment method. In view of the foregoing, a benefit of present embodiments to users includes prompting the user to select the payment method that most benefits the user, which may include achieving a result desired by the user (e.g., a contribution to a charitable cause that is preferred by the user). It should be noted that rewards or reward data include discounts, cash back, prizes, points, gifts, and so forth.

FIG. 1 illustrates a geolocation purchasing system 10, in accordance with embodiments described herein. The geolocation purchasing system 10 includes a personal device 12 (e.g., cellular device, smartphone, tablet, wearable device, smart watch, electronic key fob) that is configured to store payment method information (e.g., debit card number, credit card number, card expiration date, billing address, card security code). The payment method information may include information required for an authorization request of a transaction. In some embodiments, the personal device 12 includes a software application (e.g., mobile wallet application) that is pre-installed on the personal device and stores the payment method information. In some embodiments, the application is downloaded and installed via an application store. The application may include a user interface 14 displayed on the personal device 12. The user interface 14 may enable input, editing, or deletion of payment method information by, for example, a user 22. The user interface 14 may include additional features associated with a mobile wallet application. For example, the additional features may include a settings page for setting up display preferences, payment preferences, rankings of rewards and contributions, default payment methods, alerts, etc. The rankings of rewards and contributions may be utilized by the geolocation purchasing system 10 to identify a preferred payment method. For example, a discount of 1% of a purchase price may be available via a first payment card and a contribution of 3% of a purchase price to a charity may be available for a second payment card. Preference settings established by the user may facilitate identifying which payment card to used based on such data.

The user interface 14 may display a payment method identifier 16 (e.g., a name, a custom name, an icon) for at least some of the payment methods stored in the application. As set forth above, to make a payment, the user 22 selects a payment method and moves the personal device 12 proximate to a point-of-sale terminal 18 (e.g., cash register). The user interface 14 may be configured to display a list of payment method identifiers 16 to the user 22 before the user selects the payment method, such that the user 22 may select the payment method from the list of payment method identifiers 16. The application may be configured to turn on the display 20 of the personal device 12 to show the list of payment method identifiers 16 based on the location of the personal device 12. The location of the personal device 12 in a store or proximate a sales terminal, for example, may be an indication that the user is initiating or will likely soon initiate a transaction, such that the application may be configured to turn on the display 20 of the personal device 12 when the personal device 12 is identified as being in such a location. This may create efficiencies for a smooth transaction process (e.g., avoiding requiring the user to perform certain activation steps) while also notifying the user to the opportunity of using the application for payment. In some embodiments, the personal device 12 may output some other transaction notification, such as a sound effect (e.g., alarm, ring, beep) or haptic feedback (e.g., vibration) based on the location of the personal device 12.

In some embodiments, the personal device 12 may periodically receive a geolocation of the personal device 12 via a location sensor to determine the location of the personal device 12. The personal device 12 may determine that personal device 12 is in or near a retailer (e.g., grocery store) based on the geolocation. Further, based on the geolocation, the personal device may determine that the user 22 is entering the retailer, which may be an indication that the user will soon initiate a transaction. In some embodiments, locations of the point-of-sale terminals 18 (e.g., cash registers) may be provided to the personal device 12. The personal device 12 may determine that the user 22 is located proximate a point-sale-terminal 18 or moving toward a point-sale-terminal 18 and cause the application to provide an alert and/or turn on the display 20 of the personal device 12 to show the list of payment method identifiers 16. The personal device may cause the application to turn on the display 20 of the personal device 12 to show the list of payment method identifiers 16 in response to the personal device 12 being located within a predetermined proximity of the point-of-sale terminal 18. For example, the predetermined proximity may be within ten feet of the point-of-sale terminal 18, though any suitable distance is contemplated. The user 22 associated with the personal device 12 may be waiting in a line for the point-of-sale terminal 18. The line may be fifteen feet long. After the user 22 moves forward in line such that the personal device 12 is within ten feet of the point-of-sale terminal 18, the personal device 12 may determine that the personal device 12 is moving in a direction toward the point-of-sale terminal 18. Thus, the personal device 12 may turn on the display 20 and/or output a notification that enables or alerts the user 22 to view the list of payment method identifiers 16 via the user interface 14.

In some embodiments, the personal device 12 is configured to turn on the display 20 of the personal device 12 to show the list of payment method identifiers 16 based communication received from the point-of-sale terminal 18 (e.g., cash register). The point-of-sale terminal 18 may be configured to output a pre-sale signal 24 indicating items (e.g., milk, eggs, bread) scanned by the point-of-sale terminal 18 and/or a total cost of the scanned items. The personal device 12 may determine that the user 22 is initiating or will soon initiate a transaction in response to receiving the pre-sale signal 24. In some embodiments, the point-of-sale terminal 18 may output other signals 26 or provide scannable indicia (e.g., a barcode) that, when received or scanned by the personal device 12, cause the personal device 12 to turn on the display 20 and/or output a notification that enables or alerts the user 22 to view the list of payment method identifiers 16 via the user interface 14.

In addition to displaying the payment method identifiers 16, the user interface 14 may display additional information relevant to the payment method options. For example, the additional information may include available rewards or discounts, interest rates, credit limit, available balance, and/or current balance. The additional information may aid the user 22 in making an informed selection regarding the payment method. In some embodiments, the user interface 14 enables the user 22 to customize the additional information that is viewable via the user interface 14.

Moreover, the user interface 14 is configured to display prompts 28 for the user 22 indicating a recommended payment method for the retailer and/or a specific transaction. In some embodiments, the user interface 14 is configured to display the prompt 28 in response to the personal device 12 determining that the user 22 is initiating or will soon initiate a transaction. In some embodiments, the prompt 28 may be configured occupy a top layer of the user interface 14, such that the prompt 28 is viewable over the list of payment method identifiers 16. In additional or alternative embodiments, the prompt 28 includes a separate window or page in the application. The prompt 28 may include the payment method identifier 16 of the recommended payment method. Further, the prompt 28 may include a description indicating a reason for the recommendation. For example, the description may indicate that the recommended payment method has the highest discount of all of the payment methods (or lowest amount of money spent by the user) stored in the mobile wallet application.

The prompt 28 may also include interactive buttons. In some embodiments, the prompt 28 includes an accept button 30 (e.g., a selectable button labeled "YES") that is configured to select the recommended payment method and proceed with the transaction by outputting a transaction signal 34 to the point-of-sale terminal 18. The prompt 28 may also include a decline button 32 (e.g., a selectable button labeled "NO") configured to close the prompt 28, such that the user 22 may view and select a payment method from the list of payment method identifiers 16. In some embodiments, selecting the decline button 32 removes the recommended payment method from the list of payment method identifiers 16. Moreover, the prompt 28 may include options to close, resize, minimize, or maximize the prompt 28 for the convenience of the user 22.

Figure 2:
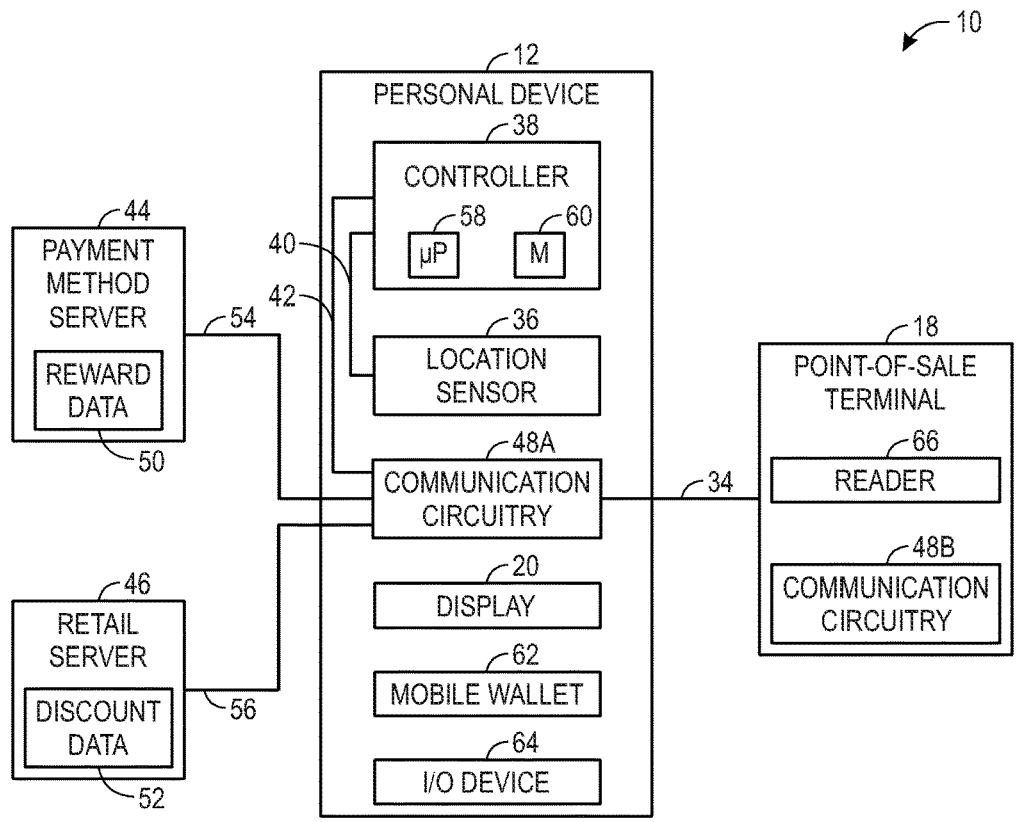
FIG. 2 illustrates a block diagram of the geolocation purchasing system of FIG. 1, in accordance with embodiments described herein.

FIG. 2 illustrates a block diagram of the geolocation purchasing system of FIG. 1, in accordance with embodiments described herein. The geolocation purchasing system 10 includes the personal device 12 (e.g., cellular device, smartphone, tablet, wearable device, smart watch, electronic key fob). The personal device 12 may determine a recommended payment method and/or prompt a user to select or confirm the recommended payment method. The personal device 12 may be configured to determine the recommended payment method based at least in part on a received geolocation of the personal device 12 and associated rewards for using certain payment methods. For example, the location may be identified as corresponding to a particular store and a particular payment method may have an incentive that rewards its use more than other payment methods. Further, certain preferences of a user may be taken into account by an algorithm (e.g., part of an application) employed by the personal device 12 to weight and identify preferred potential results from the various payment methods. Thus, a ranking can be provided by personal device 12 in accordance with present embodiments. For example, a user may set a preference for cash refunds over reward points. Thus, even though a reward may technically have a higher potential monetary value, a different award (e.g., an immediate cash discount) may be indicated a preferable based on weighting factors.

The personal device 12 may include a location sensor 36 configured to determine a geolocation of the personal device 12. In some embodiments, the location sensor 36 includes a global positioning sensor (GPS). However, the location sensor 36 may include any suitable sensor or sensor assembly configured to determine the geolocation of the personal device 12. The location sensor 36 may obtain any of various types of location data and may coordinate with external systems to provide the location data, which may include a specific location (e.g., an address, store name, coordinates). The location sensor 36 may provide a geolocation signal 40 to a controller 38 of the personal device 12. The geolocation signal 40 may transmit the location data directly or indirectly to the controller 38 and the location data may be provided in any of various formats in accordance with present embodiments.

The controller 38 of the personal device 12 may be configured to receive the geolocation signal 40. Further, the controller 38 may be configured to receive data 42 from a payment method server 44 (e.g., a payment option server) and a retail server 46 via communications circuitry 48A. The communication circuitry 48A provides for wireless or wired communication. In some embodiments, the communications circuitry 48A may include antennas, radio transceiver circuits, and signal processing hardware and/or software (e.g., hardware or software filters, A/D converters, multiplexers, amplifiers). These components may facilitate communicating over wireless communication paths via Infrared (IR) wireless communication, satellite communication, broadcast radio communication, Microwave radio communication, Bluetooth communication, Zigbee communication, Wifi communication, Ultra-high frequency communication (UHF), Near field communication (NFC), and the like.

The payment method server 44 may store payment method information for multiple users. Additionally, the payment method server 44 may be configured to store reward data 50 for a particular payment method. For example, a credit card business associated with the payment method server 44 may provide a promotion for additional cash back on purchases from selected retailers when using a particular payment method (e.g., credit card) associated with the credit card business. For example, the reward data 50 may include cash back, a credit to the account corresponding to the payment method, a rebate, a gift card, a percentage off a next purchase, and so on. Data corresponding to the promotion may be stored as reward data 50 and/or the type of reward (e.g., including if the reward may immediately be used on the current purchase or if the reward may only be used on a future purchase) on the payment method server 44. Moreover, the retail server 46 may be configured to store discount data 52. For example, a particular retailer may have a sale on selected goods and/or services. Data corresponding to the sale may be stored as discount data 52 on the retail server 46.

The communications circuitry 48A may be configured to receive reward signals 54 and/or the discount signals 56 that provide the respective reward data 50 and discount data 52 to the personal device 12. The communications circuitry 48A may provide reward data 50 and/or discount data 52 to the controller 38 based on the respective reward signals 54 and/or discount signals 56. The controller 38 may include a processor 58 and a memory device 60. The processor 58 may be any suitable type of computer processor or microprocessor capable of executing computer-executable instructions. In some embodiments, the processor 58 may include multiple processors that may perform operations of geolocation purchasing system 10.

The memory device 60 may include one or more tangible, non-transitory, machine-readable media. It should be noted that non-transitory indicates that the media is tangible and not merely a signal. By way of example, such machine-readable media can include random access memory (RAM), read-only memory (ROM), erasable programmable read-only memory (EPROM), electrically erasable programmable read-only memory (EEPROM), optical disk storage, magnetic disk storage or other magnetic storage devices, or any other suitable medium that can be used to carry or store desired program code in the form of machine-executable instructions or data structures, which can be executed by the processor or by other processor-based devices. The controller 38 may be configured to store the reward data 50 and/or the discount data 52 in the memory device 60. In some embodiments, the mobile wallet application is stored in the memory device 60, and the reward data 50 and/or the discount data 52 is stored in the mobile wallet application. In some embodiments, the memory device 60 stores instructions executable by the processor 58 to perform the presently disclosed techniques.

For example, the memory device 60 may store an algorithm that may be performed by the processor 58 to compare multiple the reward data 50 and/or the discount data 52 in the memory device 60 to determine that with the greatest financial benefit. That is, a first reward data may indicate a reward or value of $1.25, while a first discount data 52 may indicate a discount or value of $1. Accordingly, the processor 58 may recommend, using the algorithm, the first reward data 50. In some embodiments, the user may select the recommended payment method as that which expends the least amount of money at the time of purchase. For example, some rewards or discounts may be in the form of a rebate that may be paid at some time in the future. Other rewards or discounts may be applied to future purchases only at the retailer that the original purchase was made. As an example, the first reward data 50 indicative of a reward of $1.25 may be in the form of a mail-in rebate (and, as such, may only be realized in the future), while the first discount data 52 indicative of a discount of $1 may be used immediately. Accordingly, the processor 58 may recommend, using the algorithm, the first discount data 52, even though the first reward data 50 has a greater overall financial benefit, since the first discount data 52 expends less money at the time of purchase. In some cases, the reward data 50 may be in the form of a percentage off a future purchase. In such cases, the processor 58 may determine, using the algorithm, an average purchase amount (e.g., of the user, of an average user, of the user at that particular retailer, of the average user at that particular retailer), and estimate the savings amount based on applying the percentage against the average purchase amount. The processor 58 may then use this estimated savings amount as the reward data 50 when comparing against other reward data 50 and/or discount data 52.

In some embodiments, the algorithm may use a weighted system to evaluate rewards or discounts that may not be realized immediately. For example, the algorithm may apply a "future factor" (e.g., of 0.75) to all rewards and discounts that may not be realized immediately, apply a "present factor" (e.g., 1.0) to all rewards and discounts that may be realized immediately, and then compare the adjusted rewards or discounts to determine the recommended payment method. Using the example above, because the first reward data 50 indicative of a reward of $1.25 may only be realized in the future, the adjusted first reward is $1.25× 0.75=$0.94. Because the first discount data 50 indicative of a discount of $1 may be used on the present purchase, the adjusted first discount is $1×1.0=$1. As such, the processor 58 may recommend, using the algorithm, the first discount data 50 since it has the greater financial benefit. It should be understood that the future factor and present factor may be any suitable numbers, though the present factor may be greater than the future factor assuming the user prefers rewards and/or discounts to be immediately applicable to the present purchase. Moreover, in some embodiments, the future factor and present factor may be set by the user to reflect their preferences.

In this manner, the processor 58 of the personal device 12 may be configured to determine the recommended payment method based at least in part on the geolocation signal 40, the reward data 50, and/or the discount data 52. Advantageously, the processor 58 may enable improvements in computer-related technologies by decreasing the number of read accesses (e.g., lookups) of the reward data 50 and/or discount data 52 that a user may perform to compare rewards and discounts offered by the various payment methods, thus decreasing use of processing, memory, and networking resources.

The personal device 12 may include a display 20 configured to display the user interface of the mobile wallet application 62. The recommended payment choice for the user may be displayed via the user interface. Further, the display 20 may depict data, report, recommendations, or adjustments associated with software or executable code being processed by the processor 58. In one embodiment, the display 20 may be a touch display capable of receiving inputs from a user of the geolocation purchasing system 10. The display 20 may be any suitable type of display, such as a liquid crystal display (LCD), plasma display, or an organic light emitting diode (OLED) display. Additionally, in one embodiment, the display 20 may be provided in conjunction with a touch-sensitive mechanism (e.g., a touch screen) that functions as part of the user interface for the geolocation purchasing system 10.

The user may select a payment method via an input/output device 64. The input/output device 64 may include a touchscreen, a keyboard, a mouse, a microphone, sensors, input/output (I/O) modules, and so on. In some embodiments, based on user input received via the input/output device 64, the personal device 12 may be configured to perform a transaction with a point-of-sale terminal 18 (e.g., cash register). The point-of-sale terminal 18 is a hardware system configured to process payments. The point-of-sale terminal 18 may include a reader 66 (e.g., device for reading credit or debit cards). The reader 66 may be configured to read a magnetic strip of a credit card and/or debit card. The reader 66 may also be configured to read a chip of a credit card and/or debit card. The reader 66 may be configured to receive payment information such that the point-of-sale terminal 18 may process a payment. In some embodiments, the point-of-sale terminal 18 includes communication circuitry 48B. The communications circuitry 48B may be configured to receive payment information wirelessly. In some embodiments, the communications circuitry 48B is configured to receive the transaction signal 34 from the personal device 12. The transaction signal 34 may include payment information from the selected payment method. The point-of-sale terminal 18 may be configured to perform the transaction via processing the payment with the payment information received via the transaction signal 34.

Figure 3:
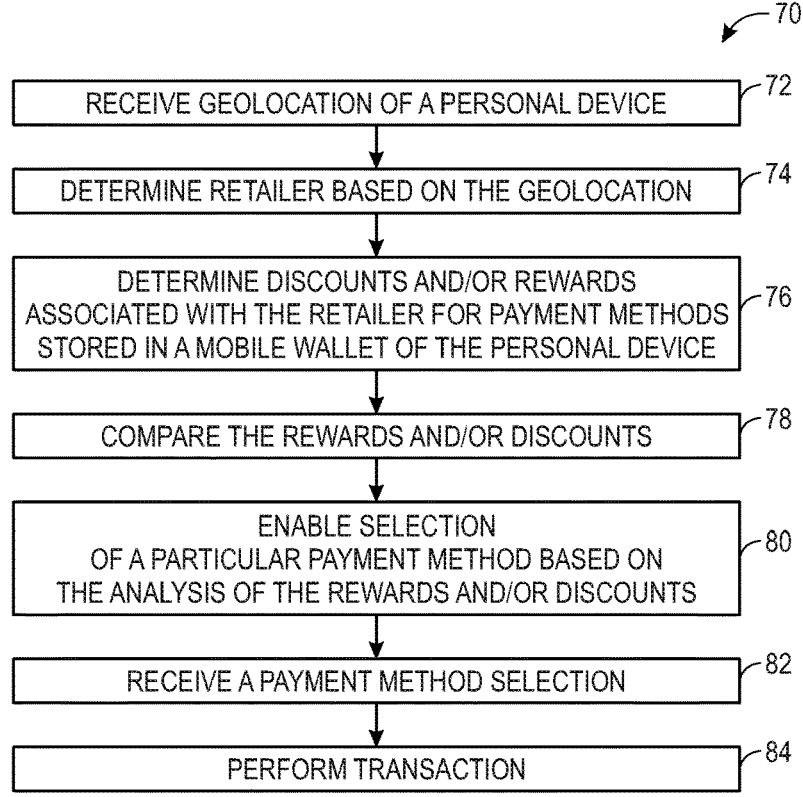
FIG. 3 illustrates a flow chart of a process for prompting selection of a particular payment method, in accordance with embodiments described herein.

FIG. 3 illustrates a flow chart of a process 70 employed by the geolocation purchasing system for prompting a user to select a particular payment method. Although the following description of the process is described in a particular order, it should be noted that the process 70 is not limited to the depicted order; and, instead, the process 70 may be performed in any suitable order, including omitting certain blocks.

As illustrated, at block 72, the geolocation purchasing system receives a geolocation of a personal device. As set forth above, the personal device may include a location sensor configured to determine a geolocation of the personal device. In some embodiments, the location sensor includes a global positioning sensor (GPS). However, the location sensor may include any suitable sensor or sensor assembly configured to determine the geolocation of the personal device. As an example, a location sensor may broadly include a sensor that detects a WIFI signal and correlates the detected signal with a location. The location sensor may provide a geolocation signal to a controller of the personal device. In other words, the location sensor may identify a location associated with the personal device and communicate data indicative of the location to a controller of the personal device for further communication or usage.

At block 74, the geolocation purchasing system determines a retailer based on the location. For example, the location sensor may be a GPS configured to provide location coordinates. The location coordinates may be provided by the GPS to the controller (e.g., a processing component) of the personal device for analysis. The location coordinates may correspond to a location of a particular retailer. For example, the controller may identify the location coordinates as corresponding to a particular retailer storefront based on a lookup table or mapping system. Thus, the geolocation system may determine that the personal device is located in, at, or near (e.g., within a threshold distance of) the particular retailer. In another example, the personal device may connect to a wireless network (e.g., WIFI) provided by the retailer. Based on the WIFI connection, the personal device may determine the retailer or a location of the retailer, and that the personal device is located in, at, or near the retailer corresponding to the wireless network.

At block 76, the geolocation purchasing system determines discounts and/or rewards associated with the retailer for payment methods stored in a mobile wallet of the personal device. As set forth above, the geolocation purchasing system may receive and store discount data from the retail server and reward data from at least one payment method server. For example, the mobile wallet may include two payment methods (e.g., a first credit card and a second credit card). The geolocation purchasing system may be configured to receive first reward data corresponding to the first credit card from a first payment method server and second reward data corresponding to the second credit card from a second payment method server. The geolocation purchasing system may determine general rewards associated with the first and second credit cards (e.g., not tied to a specific retailer or vendor) based on the respective first and second reward data. Additionally, the geolocation purchasing system may determine if additional retailer-specific rewards are associated with the first and second credit cards. The geolocation purchasing system may periodically update the rewards data (e.g., discount data) at specified times or when a defined expiration is reached. Further, the geolocation purchasing system may utilize a network search to identify available payment methods for the retailer that are not yet available in the mobile wallet but that can be added to the mobile wallet to obtain rewards (e.g., discounts).

As an example, the geolocation purchasing system may determine that the user is shopping at a first retailer, which may be used by the geolocation purchasing system to determine retailer-specific rewards. That is, the first credit card data may indicate that an additional cashback reward is available at the first retailer. Further, the second credit card data may indicate that no additional reward is available at the first retailer. Accordingly, the geolocation purchasing system may associate the first credit card stored in the mobile wallet of the personal device with the determined retailer-specific additional cashback reward.

Moreover, the geolocation purchasing system may receive the store discount data from the retailer via the retail server. However, the geolocation purchasing system may receive the store discount data from any source. The store discount data may include sales or promotions associated with the items to be purchased by the user. In some embodiments, a payment method stored in the mobile wallet of the personal device may correspond to the retailer. The geolocation purchasing system may associate the discounts (e.g., sales or promotions) with the payment method corresponding to the retailer.

At block 78, the geolocation purchasing system compares the rewards and/or discounts. In particular, the controller of the geolocation purchasing system may compare the rewards (e.g., discounts and prizes) to determine a recommended payment method for the user based on an algorithm that incorporates a factor-weighting system based on preferences (e.g., user-defined preferences). The recommended payment method may be a payment method in the mobile wallet having the most rewards, the highest discount, the overall best deal, or determined via some other suitable metric. For example, at the particular retailer, the geolocation purchasing system may be configured to recommend the overall best deal. The first credit card may provide the user with a reward of frequent flyer miles as well as a 5% discount on the purchase. The second credit card may provide the user with only a 5% discount on the purchase. Thus, the geolocation purchasing system may recommend the first credit card to the user as the payment method with the best overall deal. The mobile wallet may include an option for the user to set preferences regarding priority of types of rewards and/or an option to weigh rewards in an algorithm for selection such that the geolocation purchasing system may determine a user-customized recommended payment method. For example, variables of the algorithm may include monetary reward value (e.g., what monetary value does the reward have), type of reward (e.g., discount or points), reward accessibility (e.g., an immediate discount would be highly accessible whereas points might be less accessible because they must accumulate or be redeemed through a particular system), charitable nature of the reward, and so forth. These variables may be weighted based on user preferences (e.g., weighting values may be assigned to the rewards/discounts based on the user preferences) to enable present embodiments to better assess and recommend rewards for a user. However, even within such an algorithm, options may still be presented for confirmation by the user.

At block 80, the geolocation purchasing system enables selection of a particular payment method based on the analysis of the rewards and/or discounts. The geolocation purchasing system may prompt, via the display, the user to select the recommended payment method for the user. At block 82, the geolocation purchasing system receives a payment method selection (e.g., automatically or via a user input). In some embodiments, the mobile wallet includes a setting (e.g., option in a settings menu) for a user to authorize payment using the recommended payment method. As such, the geolocation system may automatically (e.g., without user input) select the recommended payment method. The recommended payment method may change based on the rewards and discounts available for a transaction. In some embodiments, the user may choose to select or reject the recommended payment method prompted by the geolocation purchasing system. The geolocation purchasing system may include a user interface, as set forth above, for the user to select or reject the recommended payment method. In some embodiments, the user may select another payment method after rejecting the recommended payment method. At block 84, the geolocation purchasing system performs a transaction with the payment method indicated by the payment method selection.

Figure 4:
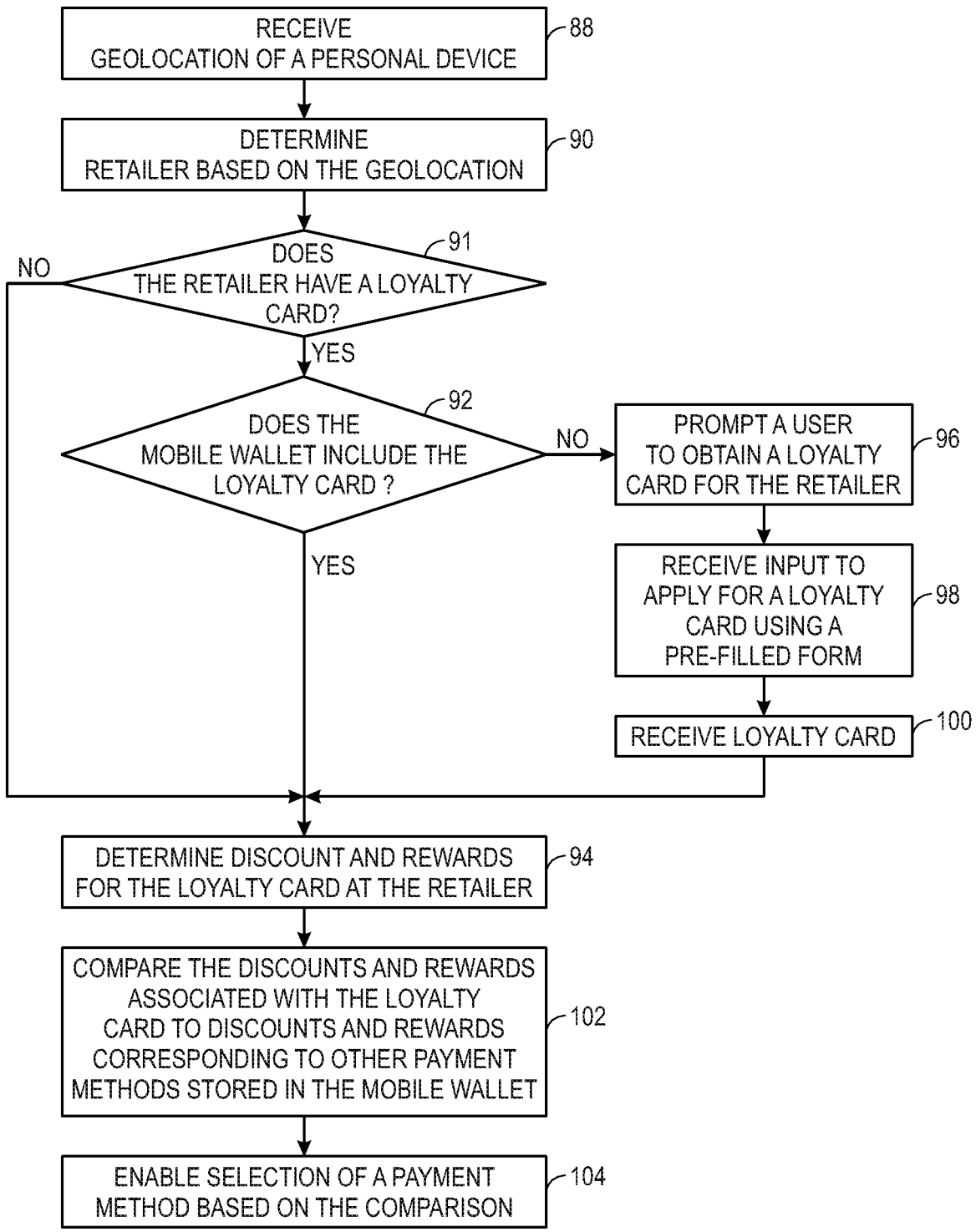
FIG. 4 illustrates a flow chart of a process for obtaining a loyalty card for a retailer at a geolocation, in accordance with embodiments described herein.

FIG. 4 illustrates a flow chart of a process 86 for obtaining a loyalty card for a retailer at a geolocation. Similar to method set forth above, at block 88, the geolocation purchasing system receives the geolocation of the personal device. Further, at block 90, the geolocation purchasing system determines the retailer based on the geolocation of the personal device. In some embodiments, the geolocation system determines whether the retailer has a loyalty card (block 91). For example, this may be done by directly communicating with a local network (e.g., via wireless communication with a point of sale device) or based on connection to a retailer website via the internet. If the retailer has a loyalty card, then the process proceeds to block 92. However, if the retailer does not have a loyalty card, then the process proceeds to block 94.

At block 92, the geolocation purchasing system determines whether a mobile wallet includes a loyalty card for the retailer. If the mobile wallet includes a loyalty card for the retailer then the process proceeds to block 94. However, if the mobile wallet does not include a loyalty card for the retailer then the process proceeds to block 96. At block 96, the geolocation purchasing system prompts the user to obtain a loyalty card for the retailer. If the user declines to obtain a loyalty card, the process proceeds directly to block 94. In some embodiments, the user may provide an input indicating that they desire to obtain the loyalty card. Thus, at block 98, the geolocation purchasing system receives the input to apply for the loyalty card using a pre-filled form. The pre-filled form may include fields for collecting information related to identifying the user (e.g., name, address, phone number). Certain fields, for which values may be known to the geolocation purchasing system, may be "pre-filled" or automatically filled by the geolocation purchasing system (e.g., without user interaction) to provide efficiency. At block 100, the geolocation purchasing system sends the fields or data associated with the pre-filled form to the user and/or the geolocation purchasing system receives the loyalty card. That is, the mobile wallet of the geolocation purchasing system receives loyalty card information (e.g. membership identification, points, balance, membership level) resulting from enrolling in the loyalty program, after which, the process proceeds to block 94.

At block 94, the geolocation purchasing system determines discounts and/or rewards (e.g., loyalty reward data) for the loyalty card at the retailer. In some embodiments, the discounts include a total discount (e.g., a $5 discount) that may be calculated from a combination of item-specific discounts for goods and/or services sought by the user. For example, each of five items sought by the user may have a $1 discount, such that the total discount is $5. The rewards for the loyalty card may include store points, punch cards, or any other suitable rewards. In some embodiments, the geolocation purchasing system may determine a monetary equivalent for loyalty card rewards of store points, punch cards, or any other suitable rewards, such that the geolocation purchasing system may compare the rewards from the loyalty card to rewards from the other payment methods (e.g., credit card, debit card, cash). For example, the rewards from the loyalty card may include store points, and the retailer may discount a purchase by the user by $10 when the user redeems 1,000 points. Thus, the geolocation purchasing system may determine that the monetary equivalent for the store points is $0.01 per store point. In some embodiments, the reward may include a coupon for a percent-off of a purchase (e.g., 10% off) when the user reaches a particular amount of points (e.g., 1,000). The geolocation purchasing system may determine the monetary equivalent for loyalty card rewards of store points by calculating an average discount from using the coupon. For example, the geolocation purchasing system may determine that the user spends an average of $100 per purchase at the particular retailer. Thus, the geolocation purchasing system may determine that for each 1,000 points that the user will save 10% off of a $100 purchase. That is, the user will save $10 per 1,000 points such that the monetary equivalent for the store points is $0.01 per store point.

At block 102, the geolocation purchasing system compares the discounts and/or rewards associated with the loyalty card to discounts and rewards corresponding to other payment methods stored in the mobile wallet. The geolocation purchasing system may determine a recommended method of payment based on the comparison between the loyalty card and each of the other payment methods stored in the mobile wallet. As set forth above, the recommended payment method may be a payment method in the mobile wallet having the most rewards, the highest discount, the overall best deal, or determined by some other suitable metric. In some embodiments, the mobile wallet may include an option for the user to set preferences regarding priority of types of rewards and/or an option to weigh rewards and/or discounts such that the geolocation purchasing system may determine a user-specific recommended payment method. For example, an algorithm may be employed to establish a common value system across payment methods and rewards, which may then be modified based on weights applied to the established values. That is, each reward may be assigned a value (e.g., a prize may be identified as having a monetary value based on available market data, a cash discount may be identified as the equivalent monetary value, a monetary value of points may be identified based on predefined tables or an analysis of available point exchanges) and then a weighting may be applied based on preferences to ascertain which options are best for the user. As a specific example, a reward for using a first credit card may include a discount of $10 whereas a reward for using a second credit card may include a $10 value donated to charity. Thus, in this example, the discounts are equal but the user may have entered a preference for charity, which would weigh the algorithm to favor the second credit card as the higher recommended payment method. If the user does not enter preferences, the algorithm may simply identify a reward of the highest estimated monetary value (or results in the lowest estimated monetary value expended by the user).

At block 104, the geolocation purchasing system enables selection of a payment method based on the comparison. In some embodiments, the geolocation system automatically selects the payment method. However, in some embodiments, the geolocation purchasing system may prompt the user to select the recommended method of payment (e.g., loyalty card, credit card, debit card).

Figure 5:
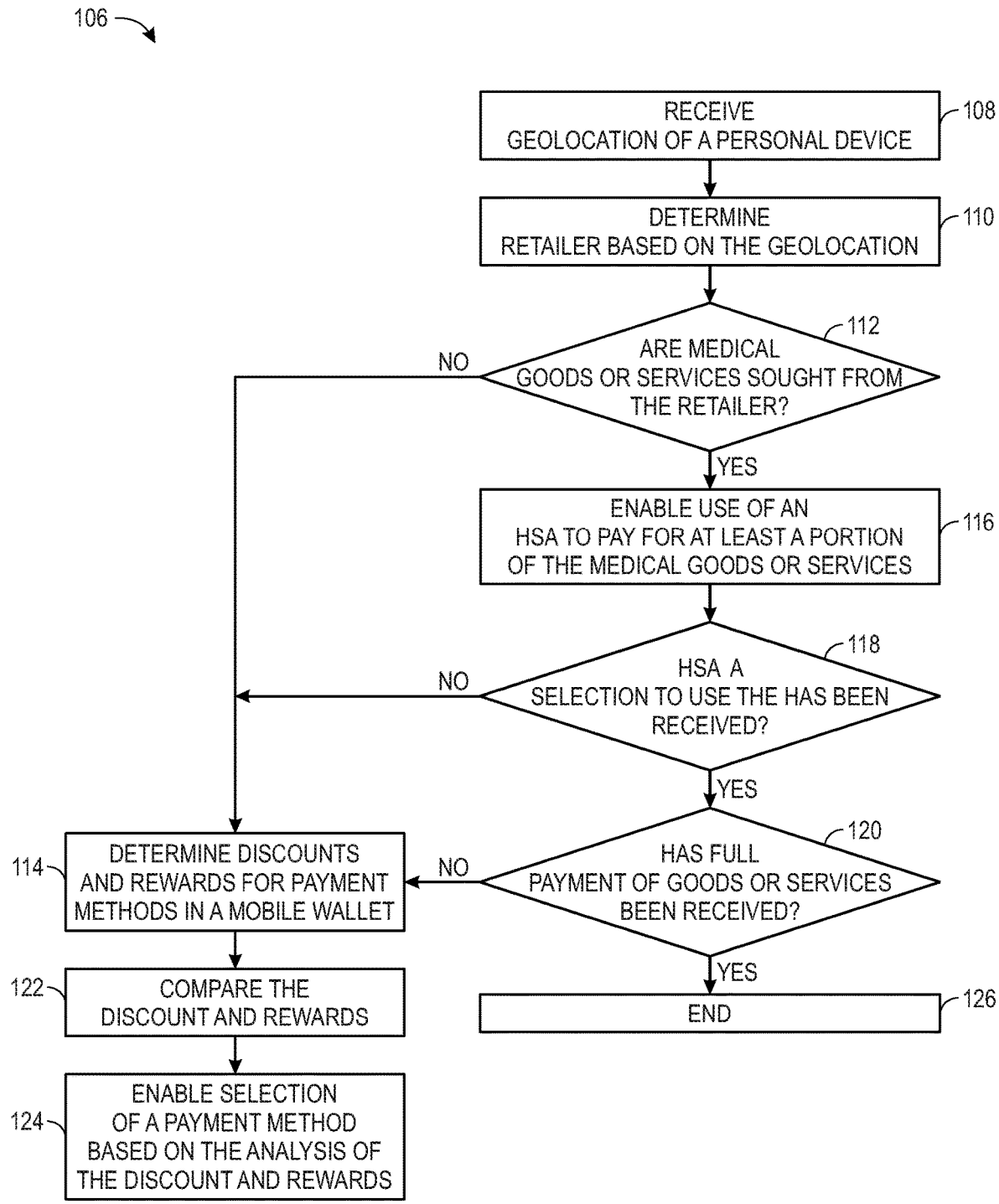
FIG. 5 illustrates a flow chart of a process for identifying whether medical goods and/or services are sought and enabling use of a health savings account for purchasing the medical goods or services, in accordance with embodiments described herein.

FIG. 5 illustrates a flow chart of a process 106 for identifying whether medical goods and/or services are sought and prompting a user to use a health savings account for purchasing the medical goods or services. Similar to the processes set forth above, at block 108, the geolocation purchasing system receives the geolocation of the personal device. Further, at block 110, the geolocation purchasing system determines the retailer based on the geolocation of the personal device.

At block 112, the geolocation purchasing system determines whether medical good or services are sought from the retailer. In some embodiments, the geolocation purchasing system may receive codes associated with goods and/or services sought by the user from the point-of-sale terminal. The geolocation purchasing system may compare the codes to a local or online database to determine the type of goods and/or services sought, such that the geolocation system may determine whether the goods and/or services sought are medical goods and/or services. If medical goods or services are not sought from the retailer then the process proceeds with block 114.

At block 114, the geolocation purchasing system determines discounts and rewards for the remaining payment methods (e.g., payment methods other than the HSA) in the mobile wallet as set forth above. The geolocation purchasing system may receive store discount data from the retail server and reward data from at least one payment method server. The geolocation purchasing system may determine discounts and rewards for each of the remaining payment methods based at least in part of the respective store discount data and the reward data.

At block 122, the geolocation purchasing system compares the discounts and rewards. As set forth above, the controller of the geolocation purchasing system may compare the rewards and discounts to determine a recommended payment method for the user. The recommended payment method may be a payment method in the mobile wallet having the most rewards, the highest discount, the overall best deal, or some other suitable option. At block 124, the geolocation purchasing system enables selection of a payment method based on the analysis of the discounts and rewards. In some embodiments, the geolocation purchasing system automatically selects the payment method and performs the transaction. In some embodiments, the geolocation purchasing system prompts the user, via the display, to select a particular payment method based on the analysis of the discounts and rewards. That is, the geolocation purchasing system prompts the user to select the recommended method of payment via the display.

Returning to block 112, if medical goods or services are sought from the retailer, then the geolocation purchasing system enables use of a health savings account (HSA) to pay for at least a portion of the medical goods or services in block 116. In some embodiments, the user may provide an input indicating that they desire to use the HSA to pay for at least a portion of the medical goods or services. Additionally or alternatively, the user may choose to pay for a portion of the medical goods or services out-of-pocket, while choosing to pay for another portion (e.g., the remaining portion) of the medical goods or services with the HSA.

At block 118, the geolocation purchasing system determines whether selection to use the HSA is received. For example, the user may select to use the HSA via the user interface. If the geolocation purchasing system does not receive user input to use the HSA, then the process proceeds with block 114. In such a case, the geolocation purchasing system may determine discounts and rewards for the payment methods in the mobile wallet as set forth above. In some embodiments, the geolocation purchasing system may determine discounts and rewards for the payment methods in the mobile wallet, other than the HAS. In additional or alternative embodiments, the HSA may offer incentives, such as discounts and/or rewards. Accordingly, the geolocation purchasing system may determine such discounts and/or rewards, and, in block 122, compare these discounts and/or rewards to those of the other payment methods in the mobile wallet. Thus, the geolocation purchasing system may enable selection of the HSA based on its discounts and/or rewards in block 124.

However, if the geolocation purchasing system receives user input to use the HSA, then the process proceeds to block 120. At block 120, the geolocation purchasing system determines whether full payment for the goods or services is made via the HSA (e.g., whether the transaction has been completed). If so, the transaction is completed, and the process ends at block 126. If full payment for the goods or services has not been received, then there are other non-medical goods and services that still need to be paid for, and the process proceeds with block 114.

Figure 6:
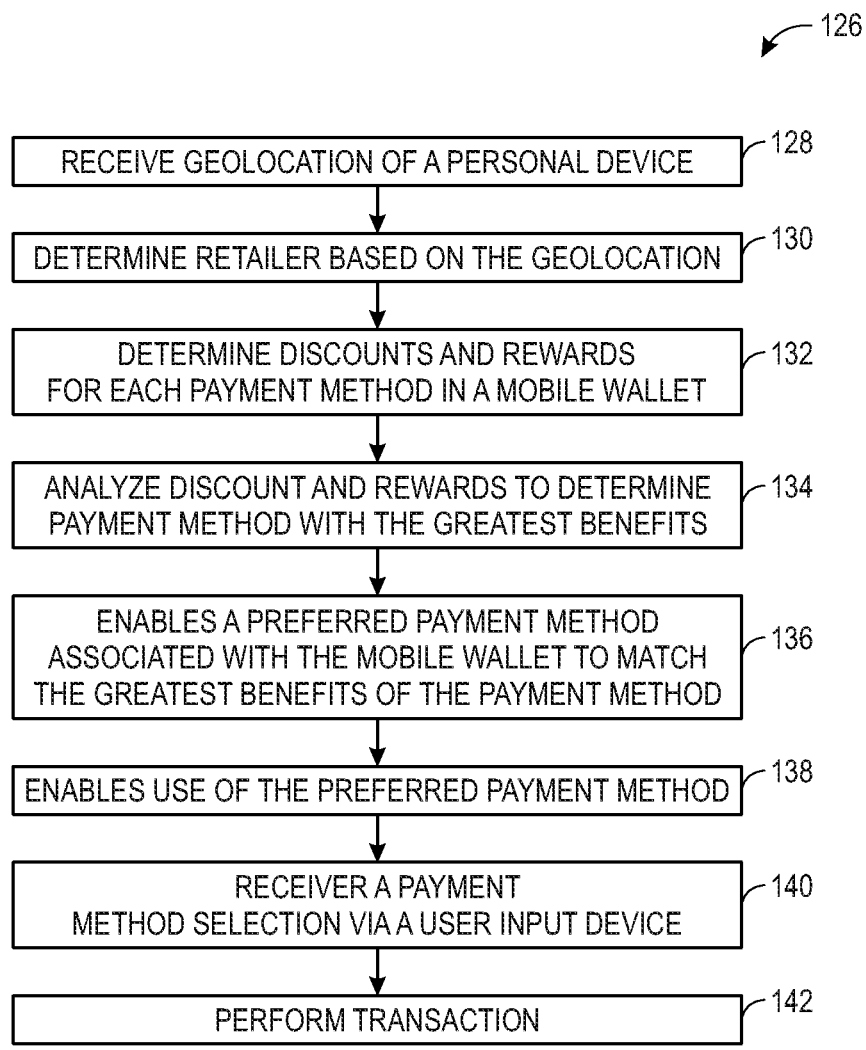
FIG. 6 illustrates a flow chart of a process enabling a preferred payment method to match benefits with other payment methods and enabling use of the preferred payment method.

FIG. 6 illustrates a flow chart of a process 126 that enables a preferred payment method to match benefits with other payment methods and enabling use the preferred payment method. Similar to the processes set forth above, at block 128, the geolocation purchasing system receives the geolocation of the personal device. Further, at block 130, the geolocation purchasing system determines the retailer based on the geolocation of the personal device. Additionally, at block 132, the geolocation purchasing system determines discounts and rewards for each payment method in the mobile wallet.

At block 134, the geolocation purchasing system analyzes discounts and rewards to determine a payment method with the greatest benefits. The geolocation purchasing system may determine the payment method with the greatest benefits is the payment method with the most rewards, the highest discount, the overall best deal, or some other suitable option. The mobile wallet may include an option for the user to set preferences regarding priority of types of rewards and/or an option to weight rewards versus discounts such that the geolocation purchasing system may determine a user specific payment method with the greatest benefits.

At block 136, the geolocation purchasing system enables a preferred payment method associated with the mobile wallet to match the greatest benefits of the payment method. That is, the geolocation purchasing system may have a preferred payment method for the customer. The preferred payment method may be associated with the mobile wallet. The preferred payment method may be configured to match the rewards and discounts (e.g., the reward or discount data) of the payment method identified by the geolocation purchasing system as having the greatest benefits such that the preferred payment method also offers the greatest benefits (e.g., equivalent benefits based on a monetary common value) to the user. In some embodiments, a loyalty card may provide the greatest benefits to the user. The loyalty card may provide store points as a reward. The geolocation purchasing system may be configured to enable the preferred payment method to match the store points of the loyalty card by providing a reward for the preferred payment method equal to the monetary equivalent, set forth above, of the store points.

At block 138, the geolocation purchasing system enables use of the preferred payment method. As the preferred payment method is configured to match the greatest benefits for each transaction made by the user, in some embodiments, the geolocation purchasing system always prompts the user to use the preferred payment method. In some embodiments, the geolocation purchasing system may recommend both the preferred payment method and the payment method having the greatest benefits. In some embodiments, the geolocation purchasing system is configured to always recommend the preferred payment method. However, the recommendation may include a note to the user that the preferred payment method matches the greatest benefits of another payment method. At block 140, the geolocation purchasing system receives a payment method selection via a user input device. At block 142, the geolocation purchasing system performs the transaction with the selected payment method. In some embodiments, the geolocation purchasing system automatically selects the preferred payment method and performs the transaction.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

While only certain features of disclosed embodiments have been illustrated and described herein, many modifications and changes will occur to those skilled in the art. It is, therefore, to be understood that the appended claims are intended to cover all such modifications and changes as fall within the true spirit of the present disclosure.

The invention claimed is:

1. A portable electronic device comprising:
a location sensor configured to determine location data indicative of a location of the portable electronic device relative to a point-of-sale terminal;
an electronic display configured to display a user interface; and
one or more memory devices and one or more processors, the one or more memory devices having a mobile wallet and instructions stored thereon, wherein the mobile wallet includes a plurality of payment options and wherein the instructions, when implemented by the one or more processors, cause the one or more processors to:
access the location data;
determine a retailer associated with the location data;
determine reward data associated with the plurality of payment options based on the retailer;
compare the reward data for the plurality of payment options to determine a recommended payment option for the retailer from the plurality of payment options;
compare the location data to a threshold distance relative to the point-of-sale terminal; and
in response to determining that the location of the portable electronic device is within the threshold distance:
cause the electronic display of the portable electronic device to display the user interface, wherein the user interface comprises a listing of the plurality of payment options, and wherein the listing comprises a plurality of selectable elements, each selectable element corresponding to a respective payment option;
receive transaction data associated with a plurality of items via the point-of-sale terminal, wherein the transaction data is indicative of a cost associated with the plurality of items, item identifiers associated with the plurality of items, a total number of items, or any combination thereof;
update the user interface to display at least a portion of the transaction data;
determine whether the mobile wallet includes a preferred payment option; and
in response to determining that the mobile wallet includes the preferred payment option:
cause first reward data associated with the preferred payment option to correlate with second reward data associated with the recommended payment option;
provide a notification via the electronic display indicative of the first reward data correlating with the second reward data;
enable selection of the preferred payment option via a first selectable element of the plurality of selectable elements to perform the transaction with the retailer; and
perform the transaction using the preferred payment option in response to the selection of the preferred payment option;
in response to determining that the mobile wallet does not include the preferred payment option:
enable selection of the recommended payment option via a second selectable element of the plurality of selectable elements to perform a transaction with the retailer; and
perform the transaction using the recommended payment option in response to the selection of the recommended payment option.

2. The portable electronic device of claim 1, wherein the instructions, when implemented by the one or more processors, cause the one or more processors to determine whether the mobile wallet includes loyalty card data for the retailer.

3. The portable electronic device of claim 2, wherein the instructions, when implemented by the one or more processors, cause the one or more processors to access loyalty reward data associated with the loyalty card data in response to determining the mobile wallet includes the loyalty card data, wherein the reward data comprise the loyalty reward data.

4. The portable electronic device of claim 2, wherein the instructions, when implemented by the one or more processors, cause the one or more processors to:
in response to determining that the mobile wallet does not include the loyalty card data, display a prompt to obtain a loyalty card from the retailer;
receive an input to apply for the loyalty card via the prompt; and
apply for the loyalty card.

5. The portable electronic device of claim 4, wherein the instructions, when implemented by the one or more processors, cause the one or more processors to receive the loyalty card data for the loyalty card including loyalty reward data associated with the loyalty card, wherein the reward data comprise the loyalty reward data.

6. The portable electronic device of claim 4, wherein the input to apply for the loyalty card comprises a pre-filled form generated by the portable electronic device based on user data stored in the one or more memory devices.

7. The portable electronic device of claim 1, wherein the instructions, when implemented by the one or more processors, cause the one or more processors to determine values based on the reward data associated with the payment options, compare the values, and indicate the recommended payment option based on the recommended payment option being associated with the reward data with a highest or a lowest of the values.

8. The portable electronic device of claim 7, wherein the instructions, when implemented by the one or more processors, cause the one or more processors to determine the values based on a monetary value correlated to the reward data for each of the payment options.

9. The portable electronic device of claim 7, wherein the instructions, when implemented by the one or more processors, cause the one or more processors to weight the values based on preferences for a reward type of the reward data for each of the payment options.

10. The portable electronic device of claim 1, wherein the instructions, when implemented by the one or more processors, cause the one or more processors to determine values based on the reward data associated with the payment options, compare the values, identify a first payment option associated with first reward data of the reward data corresponding to a highest or lowest value of the values, generate second reward data for a second payment option that matches the highest or lowest value, and indicate the second payment option as the recommended payment option.

11. A system comprising:
a payment option server storing reward data for a plurality of payment options stored thereon; and
an electronic device comprising:
a location sensor configured to determine location data indicative of a location of the electronic device relative to a point-of-sale terminal;
an electronic display configured to display a user interface; and
a controller comprising one or more memory devices and one or more processors, the one or more memory devices having a mobile wallet and instructions stored thereon, wherein the mobile wallet is configured to store a plurality of payment options, wherein the plurality of payment options comprises the payment option, and wherein the instructions cause the one or more processors to:
receive the location data determined via the location sensor;
determine a retailer associated with the location data;
receive the reward data for the plurality of payment option from the payment option server;
compare the reward data for the plurality of payment options to determine a recommended payment option from the plurality of payment options;
compare the location data to a threshold distance relative to the point-of-sale terminal; and
in response to determining that the location of the electronic device is within the threshold distance:
cause the electronic display of the electronic device to display the user interface, wherein the user interface comprises a listing of the plurality of payment options, and wherein the listing comprises a plurality of selectable elements, each selectable element corresponding to a respective payment option;
receive transaction data associated with a plurality of items via the point-of-sale terminal, wherein the transaction data is indicative of a cost associated with the plurality of items, item identifiers associated with the plurality of items, a total number of items, or any combination thereof; and update the user interface to display at least a portion of the transaction data; and determine whether the mobile wallet includes a preferred payment option;

in response to determining that the mobile wallet includes the preferred payment option:

cause first reward data associated with the preferred payment option to correlate with second reward data associated with the recommended payment option;

enable selection of the preferred payment option via a first selectable element of the plurality of selectable elements to perform a transaction with the retailer; and perform the transaction using the preferred payment option in response to the selection of the preferred payment option;

in response to determining that the mobile wallet does not include the preferred payment option:

enable selection of the recommended payment option via a second selectable element of the plurality of selectable elements to perform the transaction with the retailer; and perform the transaction using the recommended payment option in response to the selection of the recommended payment option.

12. The system of claim 11, comprising a retail server configured to store discount data associated with the retailer, wherein the instructions cause the one or more processors to:

receive the discount data from the retail server; and compare the discount data and the reward data to determine the recommended payment option.

13. The system of claim 11, wherein the instructions cause the one or more processors to compare the reward data for the plurality of payment options by assigning a value to each of the plurality of payment options and then determining a highest or lowest value of the plurality of payment options.

14. The system of claim 11, wherein the instructions cause the one or more processors to receive preference values for reward types of the rewards and time periods for receiving the rewards and then weight the preference values for comparison based on the reward types and the time periods associated with each of the values.

15. The system of claim 11, wherein the instructions cause the one or more processors to:

receive second location data determined via the location sensor, wherein the second location data is indicative of a second location of the electronic device relative to the point-of-sale terminal; and in response to determining the second location is indicative of the electronic device being closer to the point-of-sale terminal than the location:

cause the electronic display of the electronic device to display the user interface, wherein the user interface comprises a listing of the plurality of payment options, and wherein the listing comprises information associated with one or more payment options of the plurality of payment options indicative of respective reward data, respective interest rate, respective credit limit, respective available balance, respective current balance, or any combination thereof.

16. One or more tangible, non-transitory, computer-readable media comprising instructions that cause one or more processors to:

receive a location relative to a point-of-sale terminal from a location sensor;

determine a retailer associated with the location;

receive an indication that a transaction is to be performed with the retailer;

in response to determining that the transaction comprises medical goods or services, enable at least partial completion of the transaction related to the medical goods or services using a health savings account;

in response to determining that the transaction is not completed, determine rewards for a plurality of payment options stored in a mobile wallet;

compare the rewards for the plurality of payment options to determine a recommended payment option from the plurality of payment options;

compare the location to a threshold distance relative to the point-of-sale terminal;

in response to determining that the location is within the threshold distance:

cause an electronic display to display a user interface, wherein the user interface comprises a listing of the plurality of payment options, and wherein the listing comprises a plurality of selectable elements, each selectable element corresponding to a respective payment option;

receive transaction data associated with a plurality of items via the point-of-sale terminal, wherein the transaction data is indicative of a cost associated with the plurality of items, item identifiers associated with the plurality of items, a total number of items, or any combination thereof;

update the user interface to display at least a portion of the transaction data;

determine whether the mobile wallet includes a preferred payment option; and in response to determining that the mobile wallet includes the preferred payment option:

cause first reward data associated with the preferred payment option to correlate with second reward data associated with the recommended payment option;

enable selection of the preferred payment option via a first selectable element of the plurality of selectable elements to perform the transaction with the retailer; and perform the transaction using the preferred payment option in response to the selection of the preferred payment option;

in response to determining that the mobile wallet does not include the preferred payment option:

enable selection of the recommended payment option via a second selectable element of the plurality of selectable elements to perform the transaction with the retailer; and perform the transaction using the recommended payment option in response to the selection of the recommended payment option.

17. The one or more tangible, non-transitory, computer-readable media of claim 16, wherein, in response to determining that the transaction comprises medical goods or services, the plurality of payment options comprises the health savings account.

18. The one or more tangible, non-transitory, computer-readable media of claim 16, wherein, in response to determining that the transaction does not comprise the medical goods or services, the plurality of payment options excludes the health savings account.

19. The one or more tangible, non-transitory, computer-readable media of claim 16, wherein the instructions cause the one or more processors to determine that the transaction is not completed in response to determining that the transaction comprises one or more non-medical goods or services.

20. The one or more tangible, non-transitory, computer-readable media of claim 16, wherein the instructions cause the one or more processors to determine that the transaction is not completed in response to receiving an indication to not use the health savings account.

\* \* \* \* \*